US012594381B2

(12) United States Patent
Kohani et al.

(10) Patent No.: US 12,594,381 B2
(45) Date of Patent: Apr. 7, 2026

(54) SAFETY SYRINGE

(71) Applicant: K2Inov8 LLC, La Jolla, CA (US)

(72) Inventors: Kambiz Kohani, San Diego, CA (US);
Jason Swanson, Albuquerque, NM
(US)

(73) Assignee: K2INOV8, INC., Felton, DE (US)

( * ) Notice: Subject to any disclaimer, the term of this
patent is extended or adjusted under 35
U.S.C. 154(b) by 0 days.

(21) Appl. No.: 19/255,001

(22) Filed: Jun. 30, 2025

(65) Prior Publication Data

US 2026/0000836 A1     Jan. 1, 2026

Related U.S. Application Data

(60) Provisional application No. 63/666,136, filed on Jun.
29, 2024.

(51) Int. Cl.
| | |
|---|---|
| *A61M 5/24* | (2006.01) |
| *A61M 5/31* | (2006.01) |
| *A61M 5/315* | (2006.01) |
| *A61M 5/32* | (2006.01) |
| *A61M 5/34* | (2006.01) |

(52) U.S. Cl.
CPC ........ *A61M 5/2422* (2013.01); *A61M 5/2466*
(2013.01); *A61M 5/3137* (2013.01); *A61M*
*5/31505* (2013.01); *A61M 5/31535* (2013.01);
*A61M 5/3158* (2013.01); *A61M 5/31591*
(2013.01); *A61M 5/3202* (2013.01); *A61M*
*5/3245* (2013.01); *A61M 5/3257* (2013.01);
(Continued)

(58) Field of Classification Search
CPC .............. A61M 5/3137; A61M 5/2422; A61M 5/2466; A61M 2005/2403; A61M
2005/2407; A61M 2005/2433; A61M
2005/2437; A61M 2005/244; A61M
2005/2444; A61M 2005/2474; A61M
5/31505; A61M 5/31535; A61M 5/3158;
A61M 5/31591; A61M 5/3202; A61M
5/3245; A61M 5/3257; A61M 5/347
See application file for complete search history.

(56) References Cited

U.S. PATENT DOCUMENTS

| | | | | |
|---|---|---|---|---|
| 4,919,657 A | * | 4/1990 | Haber | ..................... A61M 5/24 |
| | | | | 604/234 |
| 5,451,214 A | * | 9/1995 | Hajishoreh | ............. A61M 5/24 |
| | | | | 604/242 |

(Continued)

*Primary Examiner* — Kevin C Sirmons
*Assistant Examiner* — Leah J Swanson
(74) *Attorney, Agent, or Firm* — Kenneth C. Booth;
Booth Udall, PLC

(57) ABSTRACT

A dental safety syringe with a plunger assembly, push lever
slidably coupled to the piston rod, a carpule retainer slidably
coupled to the piston rod, a barrel assembly detachably
coupled to the plunger assembly with a carpule barrel sized
to receive a carpule. A needle adapter is coupled to the
carpule barrel and a sliding barrel slidably coupled to the
carpule barrel. Finger grips extend from the sliding barrel,
and an optional trigger is positioned adjacent the finger grip.
A push lever lock is slidably coupled a finger grip. A safety
cover is detachably coupled to the sliding barrel and is
configured to extend past a syringe needle when the push
lever is in the inactive position and expose the syringe
needle when the push lever is in the inactive position.
Operable with a single hand through all of its stages of use.

20 Claims, 11 Drawing Sheets

(52) U.S. Cl.
CPC ..... *A61M 5/347* (2013.01); *A61M 2005/2407*
(2013.01); *A61M 2005/2474* (2013.01)

(56)                    References Cited

U.S. PATENT DOCUMENTS

| | | | |
|---|---|---|---|
| 5,624,400 A | 4/1997 | Firth | |
| 5,779,683 A | 7/1998 | Meyer | |
| 7,033,343 B2 * | 4/2006 | McWethy | .......... A61M 5/3257 |
| | | | 604/218 |
| 2002/0169421 A1 | 11/2002 | McWethy | |
| 2008/0086108 A1 | 4/2008 | Falkel | |
| 2018/0256819 A1 * | 9/2018 | Shaw | ................. A61M 5/3221 |
| 2021/0052818 A1 | 2/2021 | Ashraf | |

\* cited by examiner

9

120

142

9

SAFETY SYRINGE

RELATED APPLICATIONS

This application claims the benefit of and priority to U.S. provisional patent application 63/666,136, filed on Jun. 29, 2024, to Kambiz Kohani and Jason Swanson, titled "SAFETY SYRINGE", the entirety of the disclosure of which is hereby incorporated by this reference.

TECHNICAL FIELD

This document relates to a safety syringe used for treating patients. More specifically, this document relates to a safety syringe operable to treat a patient using only a single hand of the operator during the capping (covering) or uncapping (uncovering) of the needle.

BACKGROUND

Syringes are essential tools used in various medical procedures. In the dental practice, examples of use include the administration of local anesthesia, irrigation of the oral cavity, and aspiration of fluids. In dentistry, these devices are designed to deliver precise amounts of anesthetic solutions, medications, or other liquids to targeted areas within the oral cavity, ensuring that dental treatments are performed with minimal discomfort to the patient. Despite their widespread use and critical role in dental practice, dental syringes pose several safety concerns that can impact both patients and healthcare providers.

One significant safety issue associated with syringes is the risk of needlestick injuries. Medical professionals frequently handle sharp needles when administering local anesthesia, which increases the likelihood of accidental punctures. Needlestick injuries can lead to exposure to bloodborne pathogens, putting dental practitioners at risk of contracting serious infections such as hepatitis B, hepatitis C, and HIV. Most needle stick injuries occur when the medical professional is re-applying the safety cap on the needle.

SUMMARY

Aspects of this disclosure relate to a safety syringe comprising a plunger assembly having a thumb ring, a piston rod extending from the thumb ring, and a harpoon on an end of the piston rod, distal to the ring, a push lever circumscribing and slidably coupled to the piston rod, wherein a first arm of the push lever extends away from the piston rod on a left side of the piston rod and a second arm of the push lever extends away from the piston rod on a right side of the piston rod, a carpule retainer circumscribing and slidably coupled to the piston rod, the carpule retainer positioned between the harpoon and the piston push lever, and a carpule spring circumscribing the piston rod and positioned between the carpule retainer and the push lever, the carpule spring configured to bias the carpule retainer away from the push lever, wherein the plunger assembly comprising an extended position wherein the thumb ring is fully extended and a compressed position wherein the thumb ring is fully compressed, a barrel assembly detachably coupled to the plunger assembly, the plunger assembly positioned inside a first end of the barrel assembly, the barrel assembly having a carpule barrel sized to receive a carpule, a needle adapter threadedly coupled to the carpule barrel at an end of the carpule barrel distal to the plunger assembly, a sliding barrel circumscribing a portion of the carpule barrel and slidably coupled to the carpule barrel, a first finger grip extending from the sliding barrel on a left side of the sliding barrel and second finger grip extending from the sliding barrel on a right side of the sliding barrel, each of the first finger grip and the second finger grip having a first side closest to the push lever and a second side farther away from the push lever compared to the first side, a trigger, positioned adjacent to the second side of the first finger grip and pivotably coupled to and extending through a finger grip collar connecting the first finger grip to the second finger grip, the trigger comprising an actuator at a first end closest the second side of the first finger grip and a latch at a second end of the trigger that extends through the sliding barrel and selectively engages with a corresponding latch of the carpule barrel, and a push lever lock slidably coupled to the first side of the second finger grip, the push lever lock having a sloped leading edge, biased to a locked position, and configured to engage with the push lever when the push lever is pushed into an active position where the first arm and the second arm are, respectively, in contact with the first finger grip and the second finger grip, and a safety cover detachably coupled to the sliding barrel distal to the plunger assembly and is configured to extend past a syringe needle attached to the needle adapter when the push lever is in the inactive position and expose the syringe needle when the push lever is in the inactive position, wherein the safety syringe is manipulatable with a single hand from a first state in which the push lever is in the inactive position, to a second state in which the push lever is in the active position and the needle is exposed, to a third state in which contents of the carpule is expelled, and to a fourth state in which the push lever is retracted from the active position to the inactive position after the contents of the carpule is expelled.

Particular embodiments may include one or more of the following features. The needle adapter may be configured to threadedly secure a syringe needle to the barrel assembly. The needle adapter may further include an adapter hub configured to threadedly engage with the barrel assembly and separately engage with the syringe needle. The barrel assembly may further comprise a spring assembly coupled to the sliding barrel, the spring assembly having a spring barrel, a spring positioned within the spring barrel coupled to a pair of stoppers positionally connected to the carpule barrel at a first end and to the sliding barrel at a second end, wherein the spring is configured to be compressed when the push lever is moved from the inactive position to the active position to bias the push lever to the inactive position.

Aspects of this disclosure relate to a safety syringe comprising a plunger assembly having a thumb ring, a piston rod extending from the thumb ring, a harpoon on an end of the piston rod, distal to the ring, a push lever slidably coupled to the piston rod, a carpule retainer slidably coupled to the piston rod and biased away from the push lever, the carpule retainer positioned between the harpoon and the piston push lever, and a barrel assembly detachably coupled to the plunger assembly, the plunger assembly positioned inside a first end of the barrel assembly, the barrel assembly having, a carpule barrel sized to receive a carpule, a needle adapter coupled to the carpule barrel at an end of the carpule barrel distal to the plunger assembly, a sliding barrel slidably coupled to the carpule barrel, a finger grip extending from the sliding barrel and fixedly coupled to the sliding barrel, a trigger pivotably coupled to the carpule barrel between the finger grip and the needle adapter, and a push lever lock coupled to the finger grip at a side of the sliding barrel, and a safety cover detachably coupled to the sliding barrel distal to the plunger assembly and configured to extend past a syringe needle attached to the needle adapter when the push lever is in the inactive position and configured to expose the syringe needle when the push lever is in the inactive position, wherein the safety syringe is manipulatable with a single hand to move the safety syringe from a first state in which the plunger assembly is in an inactive position and the syringe needle is within the safety cover, to a second state in which the sliding barrel is moved in relation to the carpule barrel and the syringe needle is exposed, to a third state in which the syringe needle is retracted into the safety cover after contents of a carpule is expelled.

Particular embodiments may comprise one or more of the following features. The push lever may further comprise a first arm of the push lever extends away from the piston rod on a left side of the piston rod and a second arm of the push lever extends away from the piston rod on a right side of the piston rod. The plunger assembly may further comprise an extended position wherein the thumb ring is fully extended and a compressed position wherein the thumb ring is fully compressed. The safety syringe may is also be manipulatable with a single hand from a state in which the plunger assembly is moved from the extended position to the compressed position, and then the plunger assembly being moved back to the extended position from the compressed position. The finger grip may further comprise a first finger grip extending from the sliding barrel on a left side of the sliding barrel and second finger grip extending from the sliding barrel on a right side of the sliding barrel, each of the first finger grip and the second finger grip having a first side closest to the push lever and a second side farther away from the push lever compared to the first side. A trigger pivotably coupled to the carpule barrel between the finger grip and the needle adapter, wherein the trigger is positioned adjacent to the second side of the first finger grip and pivotably coupled to and extending through a finger grip collar connecting the first finger grip to the second finger grip, the trigger comprising an actuator at a first end closest the second side of the first finger grip and a latch at a second end of the trigger that extends through the sliding barrel and selectively engages with a corresponding latch of the carpule barrel. The push lever lock may be slidably coupled to the first side of the second finger grip, the push lever lock having a sloped leading edge, biased to a locked position, and configured to engage with the push lever when the push lever is pushed into an active position where the first arm and the second arm are, respectively, in contact with the first finger grip and the second finger grip. The barrel assembly may further comprise a spring assembly coupled to the sliding barrel, the spring assembly having a spring barrel, and a spring positioned within the spring barrel coupled to a pair of stoppers positionally connected to the carpule barrel at a first end and to the sliding barrel at a second end, wherein the spring is configured to be compressed when the push lever is moved from the inactive position to the active position to bias the push lever to the inactive position.

Aspects of the present disclosure relate to a safety syringe comprising a plunger assembly, a barrel assembly detachably coupled to the plunger assembly, the plunger assembly positioned inside a first end of the barrel assembly and the barrel assembly having a sliding barrel slidably coupled to a carpule barrel, and a finger grip coupled to the sliding barrel, and a safety cover detachably coupled to the sliding barrel distal to the plunger assembly, the plunger assembly configured to slidably retract a syringe needle into and slidably extend the syringe needle past a distal end of the safety cover, wherein the safety syringe is manipulatable with a single hand to move the safety syringe from a first state in which the plunger assembly is in an inactive position and the syringe needle is within the safety cover, to a second state in which the sliding barrel is moved in relation to the carpule barrel and the syringe needle is exposed, to a third state in which the syringe needle is retracted into the safety cover after contents of a carpule is expelled.

Particular embodiments may include one or more of the following features. The plunger assembly may further comprise a thumb ring, a piston rod extending from the thumb ring, a harpoon on an end of the piston rod, distal to the ring, a push lever circumscribing and slidably coupled to the piston rod, a carpule retainer circumscribing and slidably coupled to the piston rod, the carpule retainer positioned between the harpoon and the piston push lever, and a carpule spring circumscribing the piston rod and positioned between the carpule retainer and the push lever, the carpule spring configured to bias the carpule retainer away from the push lever. The safety syringe may be manipulatable with a single hand from a state in which the push lever is in the inactive position to the push lever being in the active position and then the push lever being moved from the active position to the inactive position. The plunger assembly may further comprise an extended position wherein the thumb ring is fully extended and a compressed position wherein the thumb ring is fully compressed. The safety syringe may also be manipulatable with a single hand from a state in which the plunger assembly is moved from the extended position to the compressed position, and then the plunger assembly being moved back to the extended position from the compressed position. The safety cover may be configured to extend past a syringe needle attached to the needle adapter when the push lever is in the inactive position and expose the syringe needle when the push lever is in the inactive position. The barrel assembly may be detachably coupled to the plunger assembly, the plunger assembly positioned inside a first end of the barrel assembly, the barrel assembly having a carpule barrel sized to receive a carpule, a needle adapter threadedly coupled to the carpule barrel at an end of the carpule barrel distal to the plunger assembly, a sliding barrel circumscribing a portion of the carpule barrel and slidably coupled to the carpule barrel, a finger grip circumscribing a portion of and extending from the sliding barrel and fixedly coupled to the sliding barrel, a trigger position pivotally coupled between the finger grip and the needle adapter, adjacent to the sliding barrel, and a push lever lock slidably coupled to the finger grip proximal to the thumb ring and proximal to a side of the sliding barrel opposite the trigger. The barrel assembly may further comprise a spring assembly coupled to the sliding barrel, the spring assembly having a spring barrel, a spring positioned within the spring barrel coupled to a pair of stoppers positionally connected to the carpule barrel at a first end and to the sliding barrel at a second end, wherein the spring is configured to be compressed when the push lever is moved from the inactive position to the active position to bias the push lever to the inactive position.

The foregoing and other aspects, features, and advantages will be apparent from the DESCRIPTION and DRAWINGS, and from the CLAIMS if any are included.

BRIEF DESCRIPTION OF THE DRAWINGS

Implementations will hereinafter be described in conjunction with the appended and/or included DRAWINGS, where like designations denote like elements, and.

DETAILED DESCRIPTION

Figure 1:
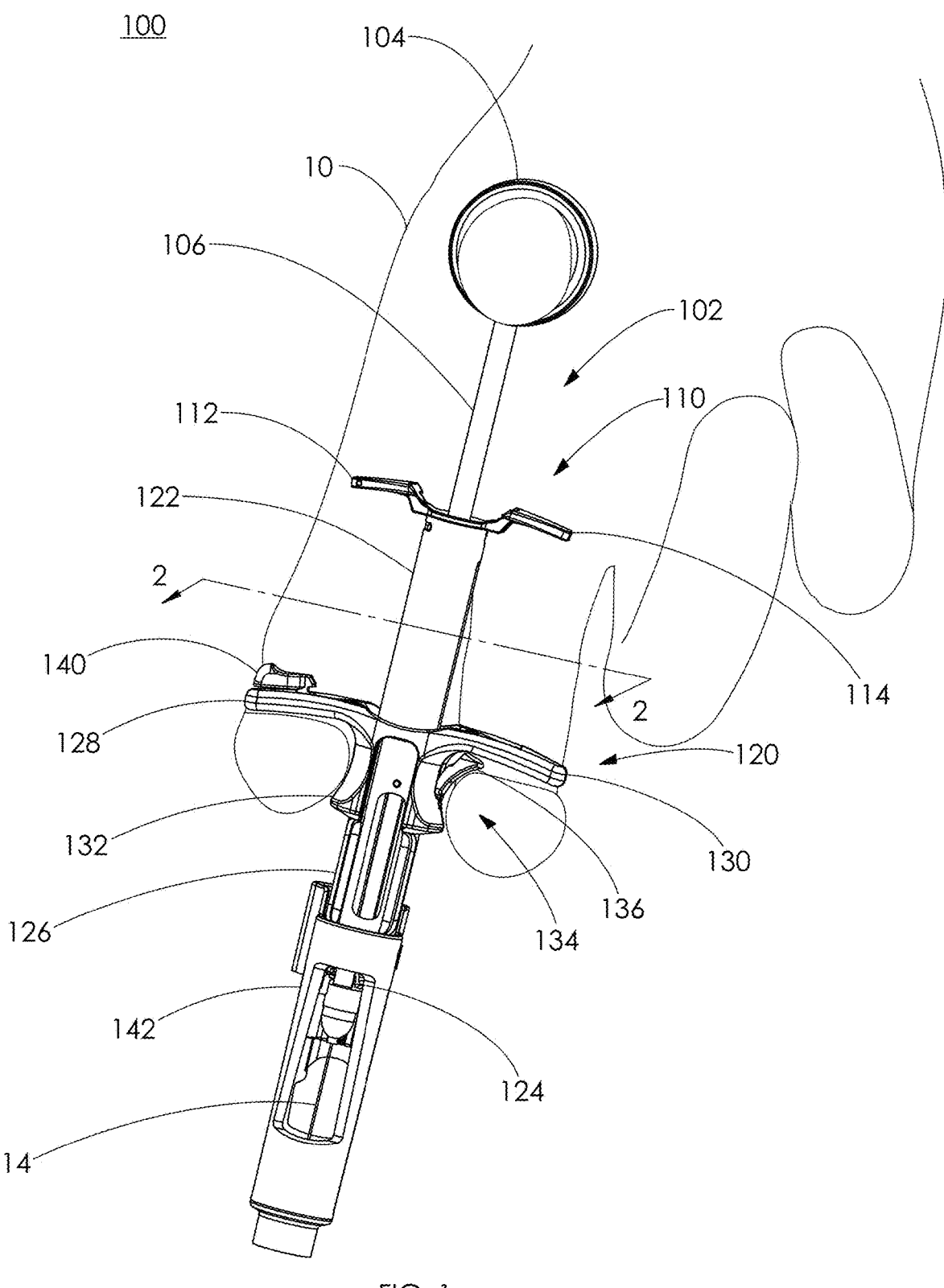
FIG. 1 is a front view of a safety syringe.

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that embodiments of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Throughout the description and claims of this specification, the words "comprise" and "contain" and variations of the words, for example "comprising" and "comprises", mean "including but not limited to", and are not intended to (and do not) exclude other components.

As required, detailed embodiments of the present disclosure are included herein. It is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the disclosure to be better understood. However, they are given merely by way of guidance and do not imply any limitation.

The present disclosure may be understood more readily by reference to the following detailed description taken in connection with the accompanying figures and examples, which form a part of this disclosure. It is to be understood that this disclosure is not limited to the specific materials, devices, methods, applications, conditions, or parameters described and/or shown herein, and that the terminology used herein is for the purpose of describing particular embodiments by way of example only and is not intended to be limiting of the claimed inventions. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

More specifically, this disclosure, its aspects and embodiments, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The present disclosure is related to a safety syringe. Some conventional syringes include components which require the use of two hands to operate safely, and some do not include a cover to reduce the risk of accidental injury once the disposable syringe needle is attached and exposed. Others include a separate cover that must be removed by a second hand, such as through twisting. The present disclosure provides examples of a safety syringe that allows the user to operate the safety syringe with only one hand and provides a safety cover which will cover the syringe needle until it is ready for use and cover the syringe needle once it has been used, all through the use of a single hand by the user. In some scenarios, it is beneficial for the user to operate the device with one hand as it will reduce the risk of accidental injury and allow the user to have one hand free to manipulate an environment. In some scenarios, it is also beneficial for the user to be protected before and after use of the disposable needle by a safety cover to further reduce the potential for accidental injury to the user and to the patient. Embodiments of the presently disclosed safety syringe are safer, reducing the overall risk of potentially injury from an exposed needle during the capping (covering) or uncapping (uncovering) of the needle, and significantly reduces the risk of accidental needle sticks which commonly occur during this phase of needle use. It also protects the exposed part of the needle prior to the point of insertion inside the oral cavity, the cover can stay in place up until the point of injection and quickly uncover the needle when in a safe position and out of patients sight. This reduces the anxiety and lowers the stress level of the patient, particularly with pediatric patients.

FIG. 1 illustrates an embodiment of a safety syringe 100 in a first state, in which the thumb ring 104 is in an extended position and the push lever 110 is in an inactive position. The safety syringe 100 includes a plunger assembly 102, a barrel assembly 120, and a safety cover 142. The plunger assembly 102 includes a thumb ring 104 coupled to a piston rod 106 and a push lever 110 that surrounds and is coupled to a portion of the piston rod 106. The push lever 110 has a first push lever arm 112 and a second push lever arm 114. The barrel assembly 120 includes a carpule barrel 122, a needle adapter 124 coupled to the carpule barrel 122 opposite the plunger assembly 102, and a sliding barrel 126 which is slidably coupled to and surrounds a portion of the carpule barrel 122. The barrel assembly 120 of this particular embodiment further includes a finger grip collar 132 that is coupled to the sliding barrel 126, with the finger grip collar 132 being coupled to both a first finger grip 128 and a second finger grip 130. In some embodiments, the finger grip collar 132 circumscribes the sliding barrel 126. In other embodiments, the first finger grip 128 and the second finger grip 130 may separately be coupled to the sliding barrel 126. The first finger grip 128 is slidably coupled to a push lever lock 140 and the second finger grip 130 is pivotally coupled to an optional trigger 134. The push lever lock 140 is biased to the locked position and includes an upper surface that is angled so that when the push lever 110 contacts the push lever lock 140, the push lever lock 140 slides to its unlocked position against the bias of a spring or other bias within the push lever lock 140 until an outer edge of the push lever 110 passes the angled upper surface and the biased push lever lock 140 biases to its locked position, securing the push lever 110 against the first finger grip 128 and the second finger grip 130. Although two finger grips 128, 130 are illustrated, only one is technically required for operation. However, two finger grips make holding and manipulating the safety syringe 100 more comfortable.

The safety cover 142 is configured to cover the syringe needle 14 in this first state. The syringe needle 14 is coupled to the carpule barrel 122 through a needle adaptor 124. A needle adapter 124 may be externally threaded to receive the internal threads of traditional syringe needles 14, or may be otherwise configured with additional components to enable simpler attachment of a syringe needle. The syringe needle 14 may be manufactured to incorporate the needle adapter 124 as one complete unit so that a separate "off the shelf" needle is not separately required. A user's hand 10 may be positioned as seen and may operate the safety syringe 100 single handedly. More specifically the thumb ring 104, the push lever 110, the trigger 134 and the push lever lock 140 may all be operated by the user's single hand without the need of the user repositioning the safety syringe 100 in the user's single hand using the user's other hand or with any other assistance.

Figure 2:
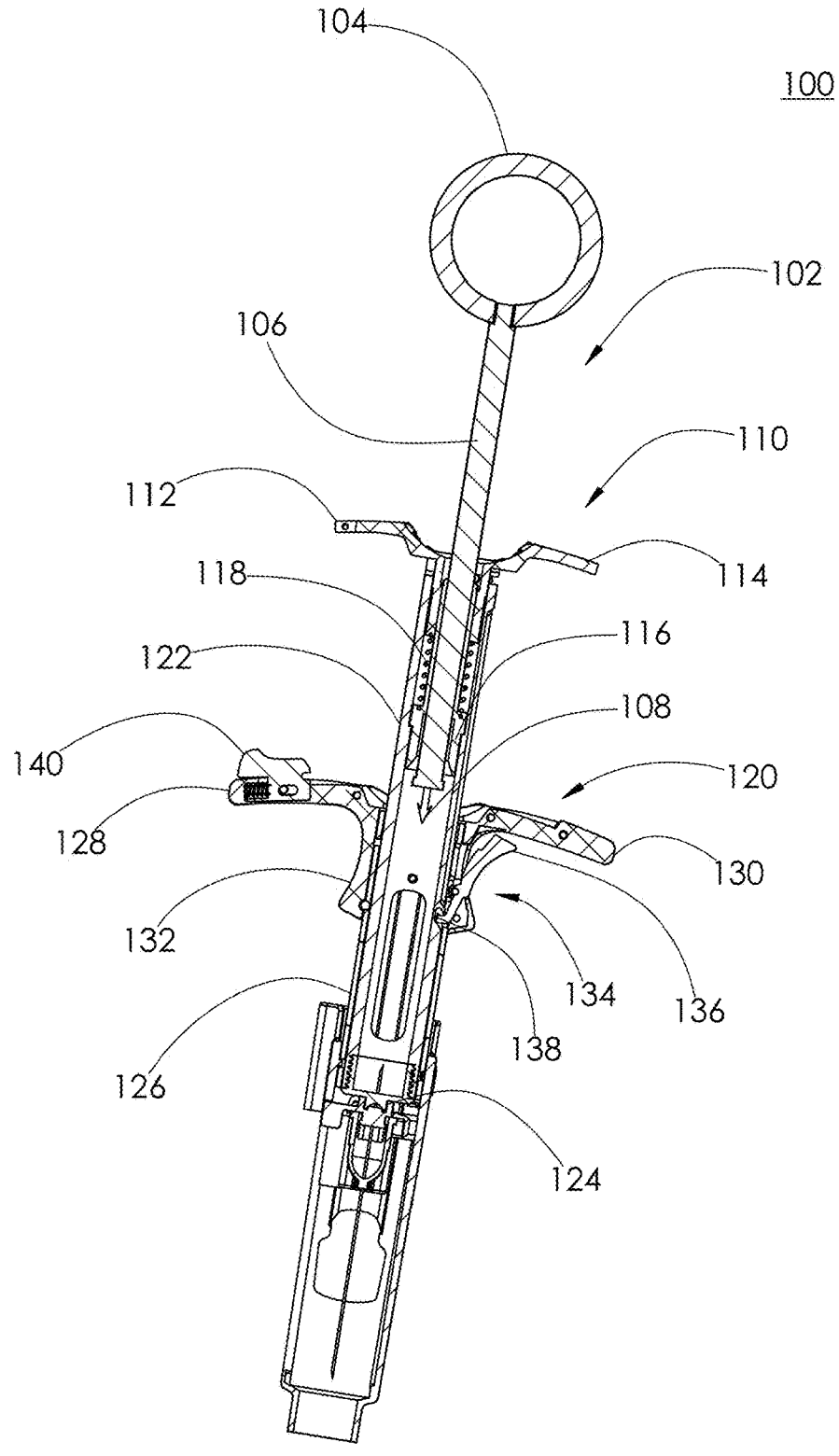
FIG. 2 is a cross-sectioned front view of the safety syringe shown in FIG. 1 taken along the section line 2-2 of FIG. 1.

FIG. 2 illustrates a cross-sectional view of the embodiment of FIG. 1 taken along cross-section line 2-2, where the safety syringe 100 is in the first state, having the thumb ring 104 is in its extended position and the push lever 110 in its inactive position as in FIG. 1. The cross-section view of FIG. 2 further illustrates internal details of the plunger assembly 102. The plunger assembly 102 includes a harpoon 108 coupled to the piston rod 106 at an end of the piston rod 106 distal to the thumb ring 104, a carpule retainer 116 circumscribing and slidably coupled to the piston rod 106 and positioned between the harpoon 108 and the push lever 110, and a carpule spring 118 circumscribing the piston rod 106 and positioned between the carpule retainer 116 and the push lever 110. The trigger 134 includes an actuator 136 and a latch 138. The latch 138 is configured to secure the carpule barrel 122 to a receiver on the sliding barrel 126 when the actuator 136 is inactive. The actuator 136 is configured to be depressed by a finger of the user's hand 10 to unsecure the latch 138 from the carpule barrel 122. In particular embodiments the trigger 134 is not required and movement of the sliding barrel 126 may be controlled solely by the user's hand.

Figure 3:
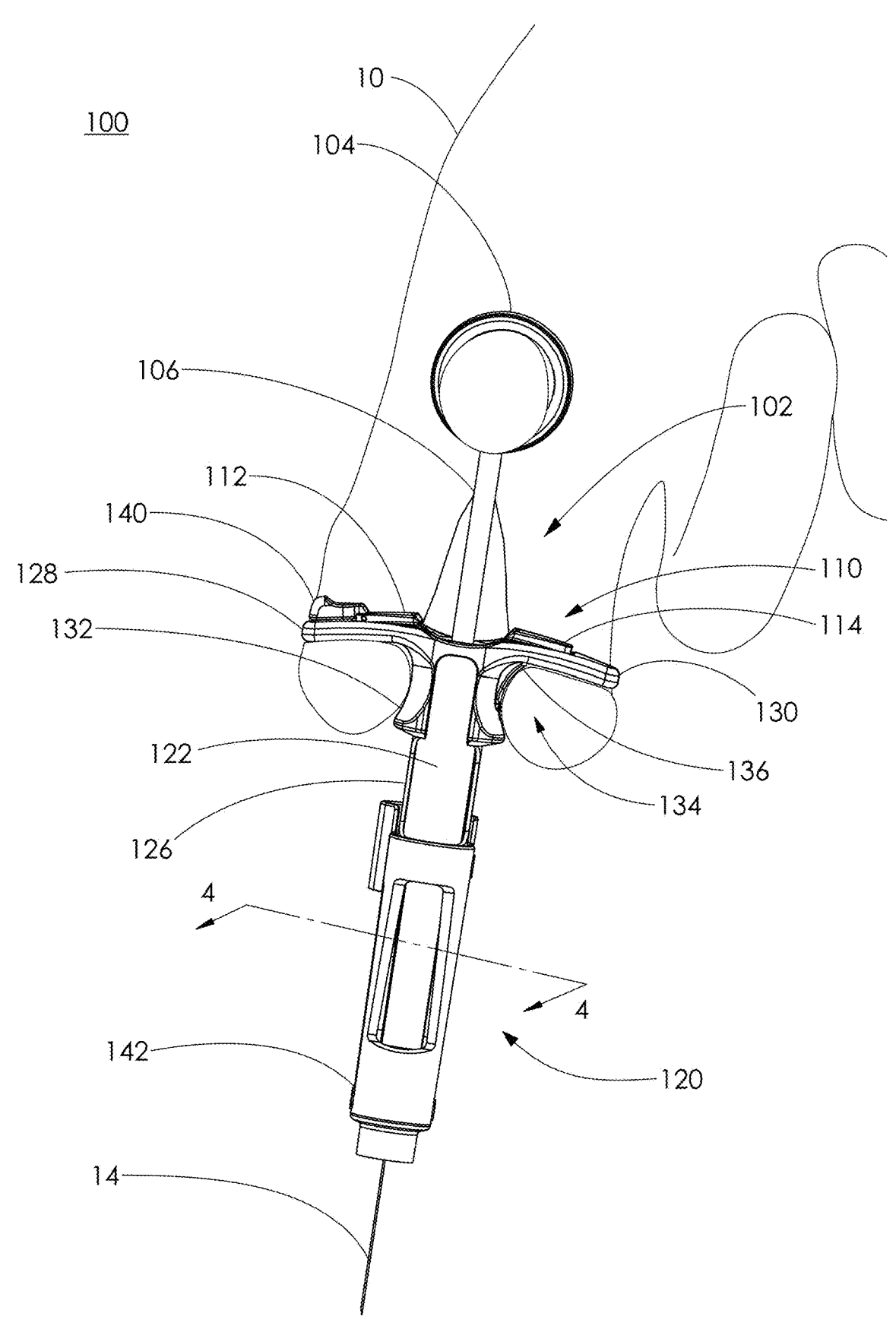
FIG. 3 is a front view of the safety syringe shown in FIG. 1.

FIG. 3 illustrates the safety syringe of FIG. 1, where the safety syringe 100 is in a second state, having the thumb ring 104 in its extended position and the push lever 110 in an active position. FIG. 3 illustrates the safety syringe 100, where the user's hand 10, such as by the user's thumb pressing the first or second push lever arm 112, 114 and squeezing the first and/or second finger grip 128, 130 with the user's fingers, has depressed the push lever 110 to be secured by the push lever lock 140. This movement is further enabled by depressing the actuator 136 and unsecuring the carpule barrel 122 from the latch 138, allowing the carpule barrel 122 to slide through the sliding barrel 126 and the safety cover 142, thereby exposing the syringe needle 14.

Figure 4:
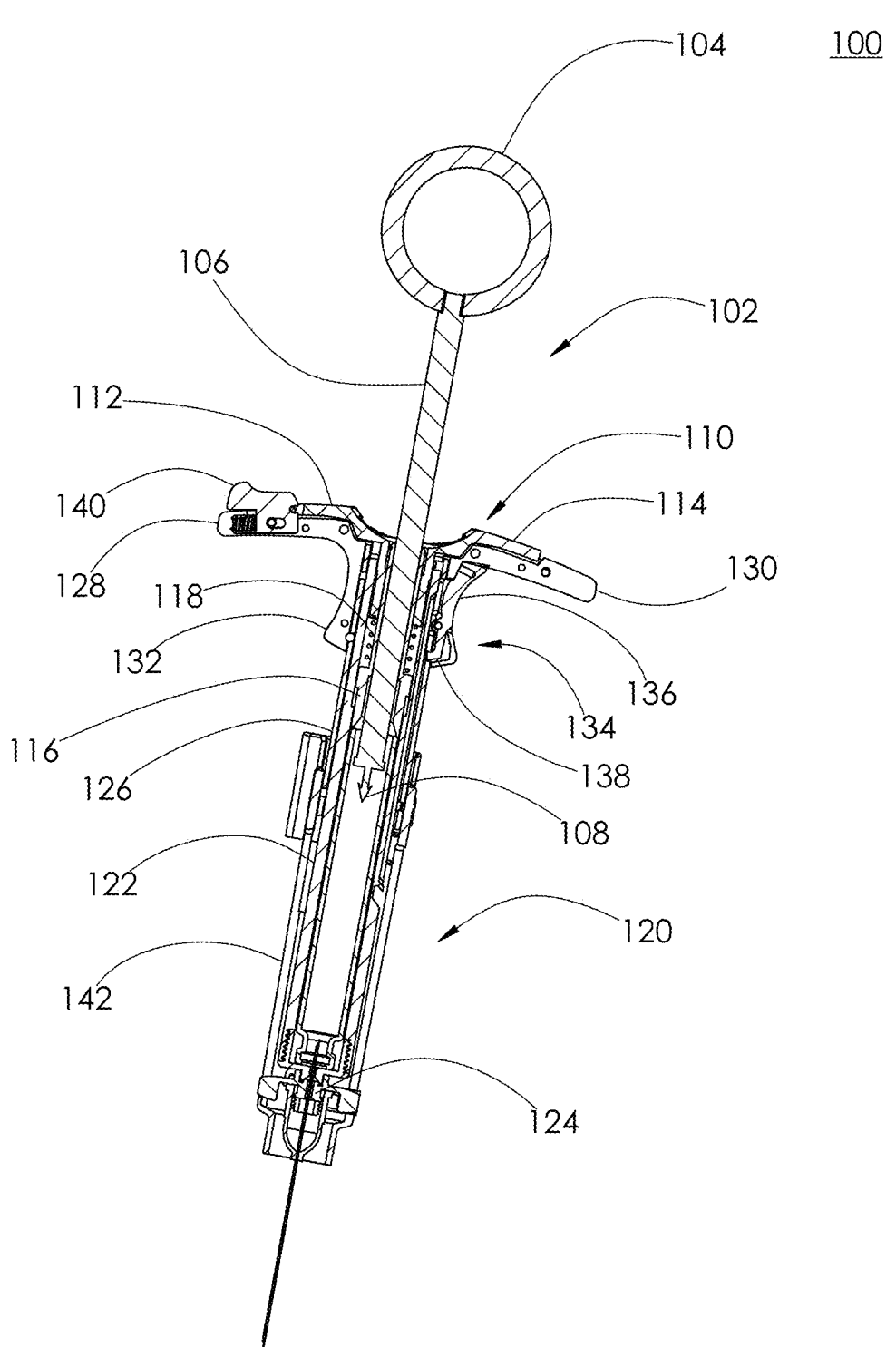
FIG. 4 is a cross-sectioned front view of the safety syringe shown in FIG. 1 taken along the section line 4-4 of FIG. 3.

FIG. 4 illustrates a cross-section view of the safety syringe of FIG. 3 along cross-section line 4-4 of FIG. 3. The safety syringe 100 in FIG. 4 is in its second state, having the thumb ring 104 in its extended position and the push lever 110 in its active position. FIG. 4 illustrates the safety syringe 100 with the latch 134 decoupled from the receiver of the carpule barrel 122 to unsecure the latch 134 so that the carpule barrel 122 can move within the sliding barrel 126 and the safety cover 142.

Figure 5:
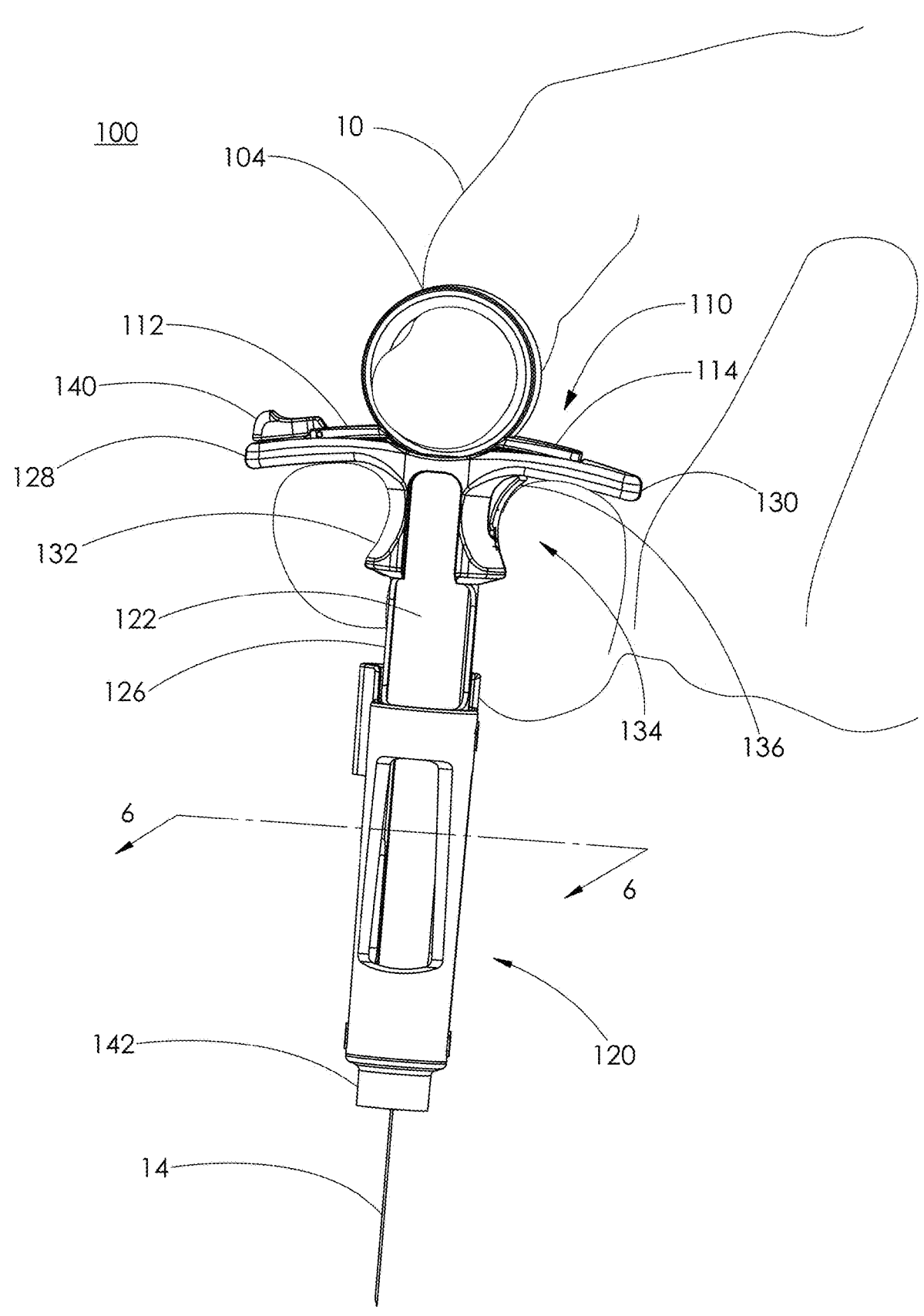
FIG. 5 is a front view of the safety syringe shown in FIG. 1.
Figure 6:
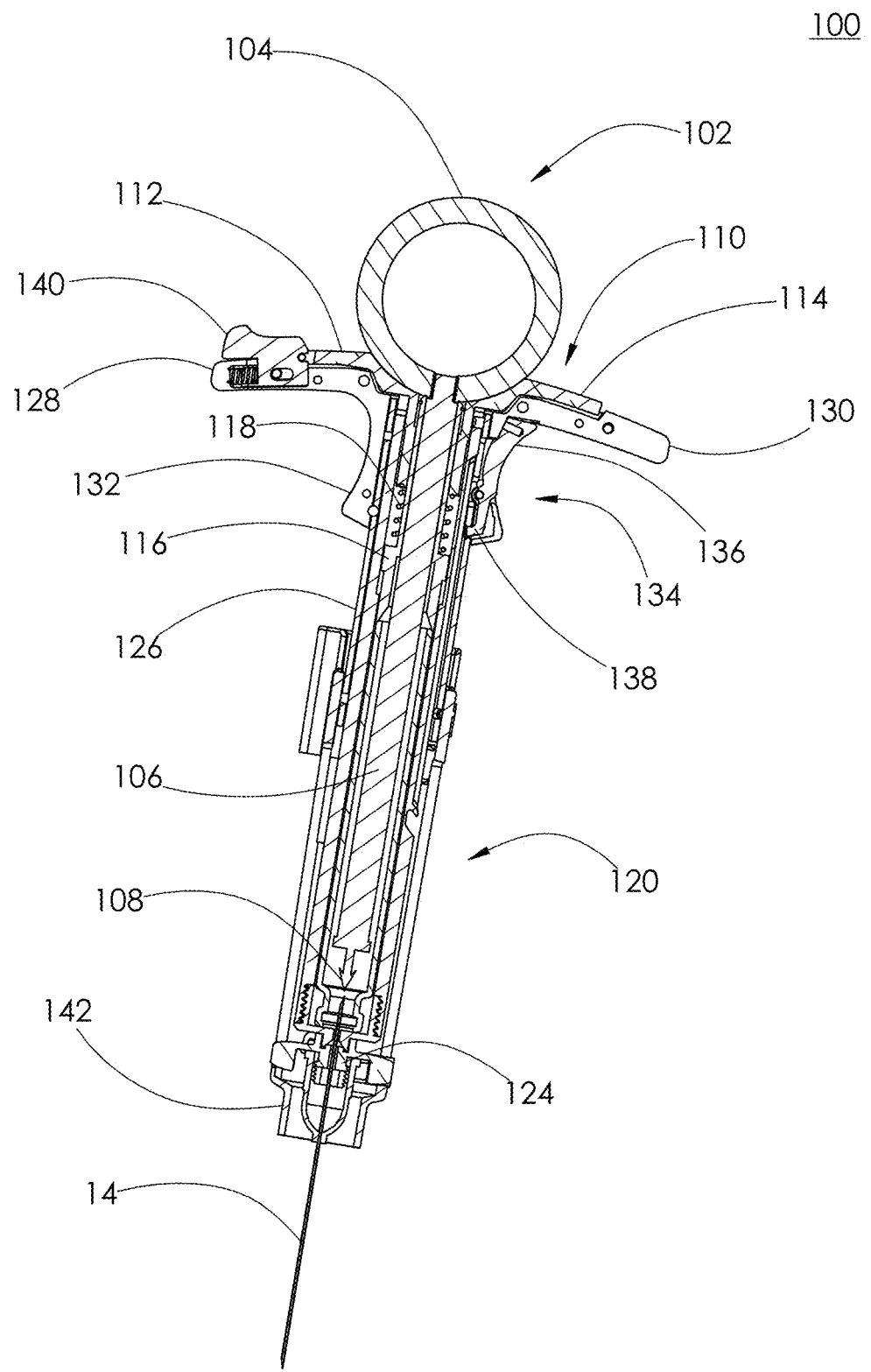
FIG. 6 is a cross-sectioned front view of the safety syringe shown in FIG. 1 taken along the section line 6-6 of FIG. 5.

FIGS. 5 and 6 further illustrate the safety syringe 100 in a third state, having the thumb ring 104 in a compressed position and the push lever 110 in its active position. FIG. 5 shows the safety syringe 100 with the user's hand 10 has depressed the thumb ring 104 in the direction of the push lever 110 in its active position. A user moves the safety syringe 100 into the third state by depressing the thumb ring 104. As this motion begins, the harpoon 108 punctures a trailing end of the carpule 12 and punctures a rubber stopper on the trailing end of the carpule 12 to secure the plunger assembly 102 to the carpule. FIG. 6 illustrates a cross-section view of the safety syringe 100 of FIG. 5 taken along cross-section line 6-6 of FIG. 5, where the harpoon 108 and the piston rod 106 are depressed in the direction of the needle adapter 124.

Figure 7:
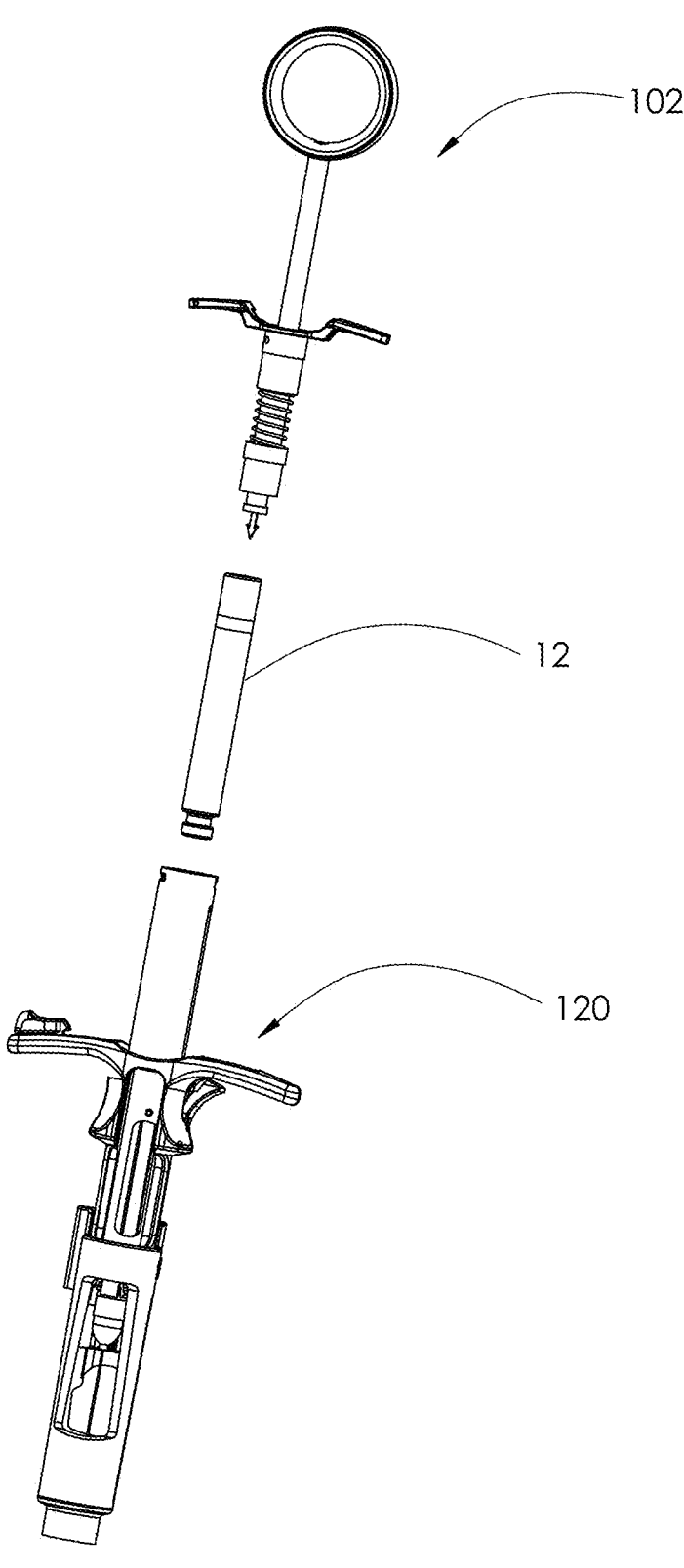
FIG. 7 is a front view of the safety syringe shown in FIG. 1 when being loaded with a new carpule.

FIG. 7 illustrates the safety syringe 100 of FIG. 1, where the safety syringe 100 is being loaded with a carpule 12. To load a carpule 12, the plunger assembly 102 is uncoupled from the barrel assembly 120, and a carpule 12 is inserted into the carpule barrel 122 at an end of the carpule barrel 122 opposite the needle adapter 124. The plunger assembly 102 is then re-inserted into the barrel assembly 120 and secured for use.

Figure 8:
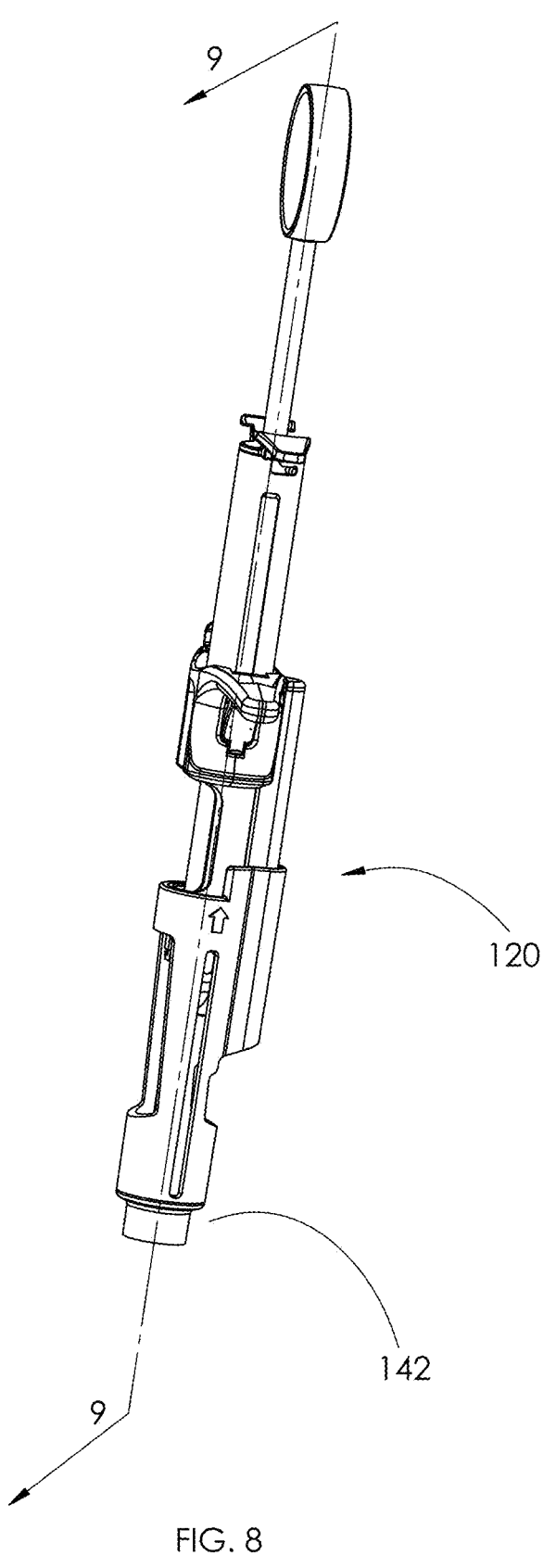
FIG. 8 is a perspective view of a portion of the safety syringe shown in FIG. 1.
Figure 9:
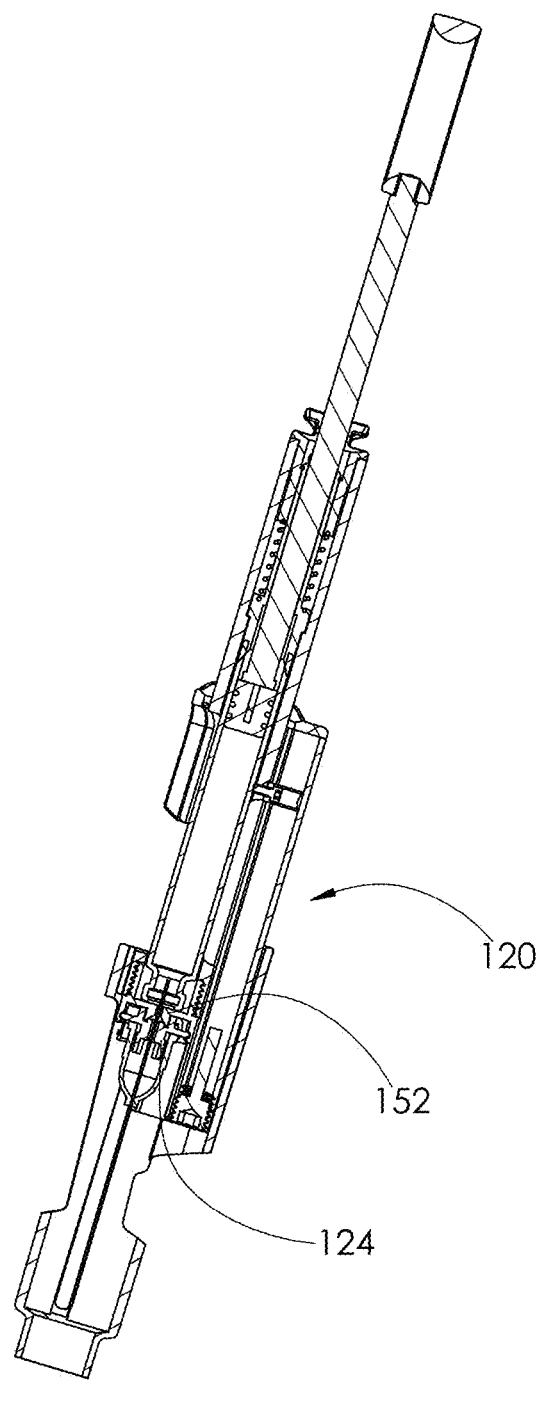
FIG. 9 is a cross-sectioned perspective view of a portion of the safety syringe shown in FIG. 1 taken along the section line 9-9 of FIG. 8.

FIG. 8 illustrates a close-up view of the safety cover 142 that is coupled to the barrel assembly 120. FIG. 9 illustrates a cross-section view of the safety syringe 100 of FIG. 8 taken section lines 9-9. The safety cover 142 is coupled to the needle adapter 124 and the needle adapter 124 includes an adaptor hub 152. The adaptor hub 152 is also coupled to the carpule barrel 122. The coupling of the adaptor hub 152 to the carpule barrel 122 may be a threaded coupling, as illustrated, or may alternatively be press-fit, welded or manufactured as one piece by combining the carpule barrel 122 with the adapter hub 152. The safety cover 142, and the needle adapter 124 with the adaptor hub 152 are configured to be coupled together, and the safety cover 142 is configured to be secured to the needle adaptor 124. In use, the adapter hub 152 and safety cover 142 may be attached to the carpule barrel 122 together. The safety cover 142 extends past a syringe needle 14. The syringe needle 14 may be coupled to the needle adaptor 124 either before the needle adaptor 124 is attached to the carpule barrel 122, or after. In some cases, this may enable easier attachment of the syringe needle 14 to the carpule barrel 122 to further reduce the risk of undesired needle sticks to the user.

Figure 10:
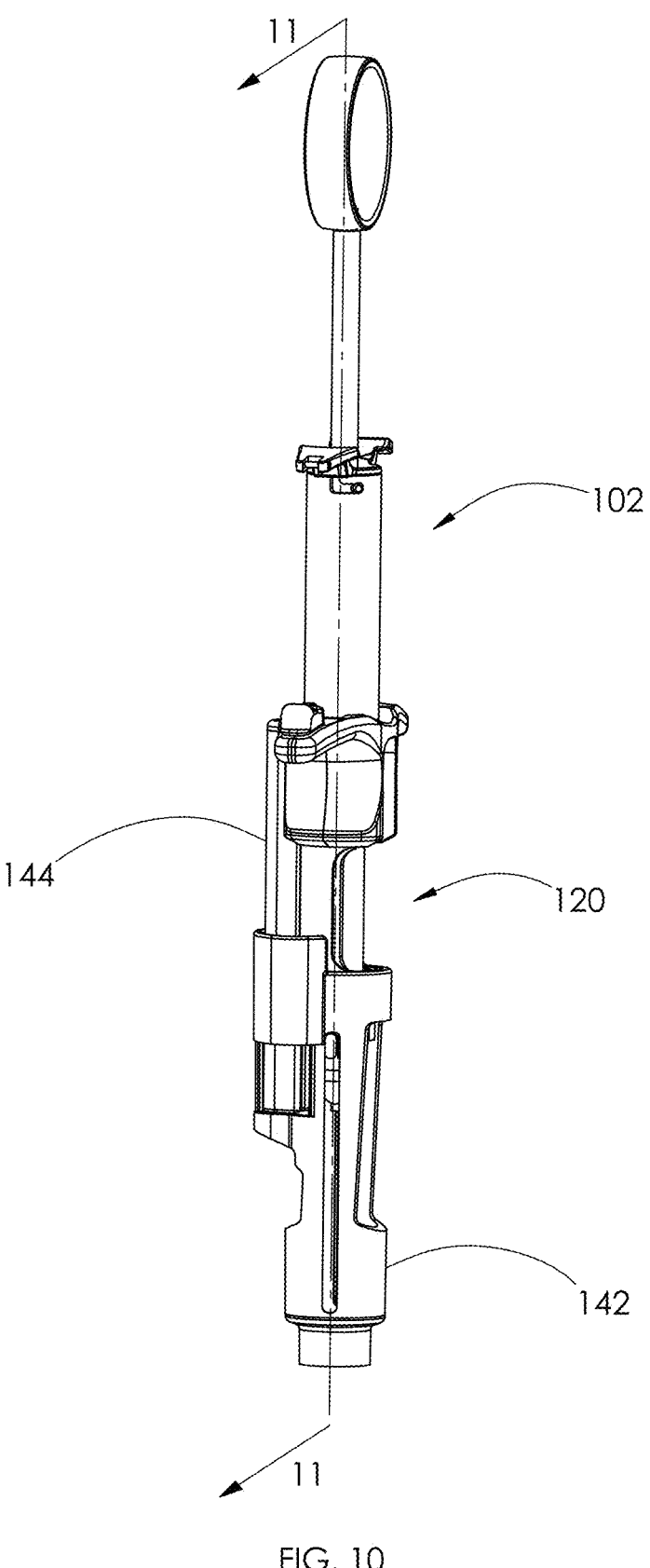
FIG. 10 is a side view of the safety syringe shown in FIG. 1.
Figure 11:
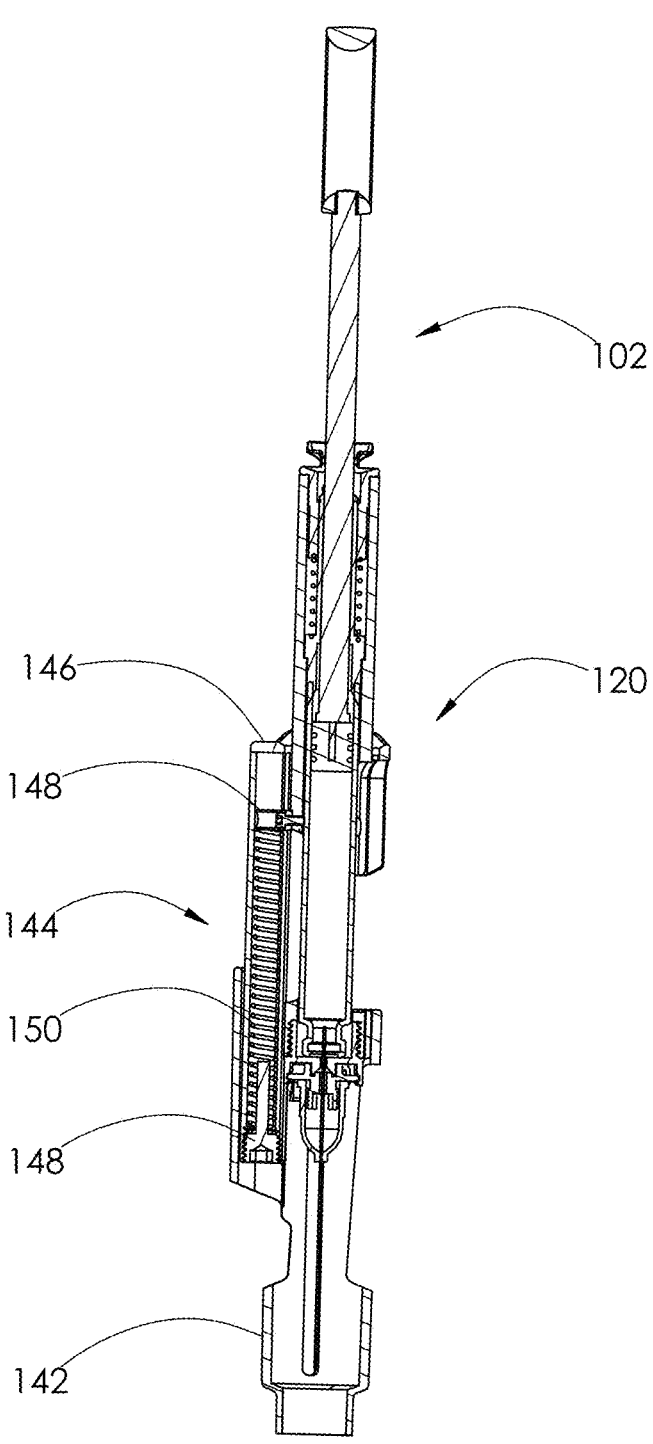
FIG. 11 is a cross-sectioned side view of the safety syringe shown in FIG. 1 taken along the section line 11-11 of FIG. 10.

FIG. 10 illustrates an optional spring assembly 144 for inclusion on the safety syringe 100. FIG. 11 illustrates a cross-section view of FIG. 10 taken along section lines 11-11. The cross-section of FIG. 11 illustrates the spring assembly 144, which includes a spring barrel 146, a spring 150 positioned within the spring barrel 146 coupled to a pair of stoppers 148 positionally connected to the carpule barrel 122 at a first end and to the sliding barrel 126 at a second end. The spring 150 of the spring assembly 144 is configured to be compressed when the push lever 110 is moved from the inactive position to the active position and is automatically secured by the push lever lock 140 in the active position. After the user depresses the plunger assembly 102, the user can unsecure the push lever lock 140 with a finger of the user's hand, and the compressed spring 150 will expand and bias the push lever 110 away from the first finger grip 128 and the second finger grip 130 to automatically return the push lever 110 to an inactive position. The safety cover 142 will then automatically cover the exposed syringe needle 14 when the push lever 110 is automatically returned to an inactive position.

In operation, a user, using only a single hand 10, can take a safety syringe 100 in its first state (FIGS. 1-2) with the syringe needle 14 safely stored within the safety cover 142, perform the following actions: 1) Press the trigger 134 with the user's finger to release the latch 138 and allow the carpule barrel 122 to slide within the sliding barrel 126 to expose the syringe needle 14 from within the safety cover 142. 2) Squeeze the push lever 110 against the first finger grip 128 and the second finger grip 130, compressing the spring 150 to the point where the push lever lock 140 engages the push lever 110 and locks the safety syringe 100 into the safety syringe 100 second state with the push lever 110 in the active position with the thumb ring 104 still extended. 3) Move the safety syringe 100 into the third state by pressing the plunger assembly 102 toward the syringe needle 14 with the user's thumb or finger in the thumb ring 104 (FIGS. 3-4) to harpoon the carpule 12 and thereafter expel the liquid from within the carpule 12 through the syringe needle 14 by pressing the thumb ring all the way to engagement with the push lever 110 (FIGS. 5-6). 4) Retract the syringe needle 14 back into the safety cover 142 by releasing the push lever lock 140 to permit the push lever 110 to move away from the first finger grip 128 and the second finger grip 130. The movement is often accomplished automatically through the compressed spring 150 expanding. With the safety cover 142 now covering the syringe needle 14, the safety syringe may be set aside and taken apart later. If all of the liquid of the carpule 12 are expelled, or if the carpule 12 contents are no longer needed, e.g. no more is needed for this patient, the carpule 12 may be removed by uncoupling the plunger assembly 102 from the barrel assembly 120. Because the harpoon 108 has harpooned the rubber stopper (also sometimes called a bung) of the carpule 12, when the plunger assembly 102 is removed from the back of the barrel assembly 120, the carpule 12 comes with it and is easily removed by a user's fingers. With conventional front-loading or side-loading syringes, it is often very difficult for a person to remove the carpule because the person's fingers do not fit within the carpule barrel if the carpule is stuck. The safety cover 142 with its enclosed syringe needle 14 safely attached to the adaptor hub 152, the safety cover 142 can be uncoupled from the carpule barrel 122 and disposed of, without risk of the user or the patient being stuck by the needle.

Embodiments of the present disclosure enable single-handed operation of a safety syringe as described above to better protect medical professionals during providing injections to a patient. Particularly for those in the dental field, where working within a patient's mouth often requires use of the user's other hand to hold other equipment or hold the patient's mouth open, safe single-handed operation of the syringe is a great advantage compared with conventional syringes that do not maintain the syringe needle covered prior to actual use, require two hands to operate, and cannot return to a safe position with the syringe needle covered without two hands or assistance from another medical professional.

Many additional implementations are possible. Further implementations are included within the CLAIMS.

It will be understood that implementations of the safety syringe include but are not limited to the specific components disclosed herein, as virtually any components consistent with the intended operation of various safety syringes may be utilized. Accordingly, for example, it should be understood that, while the drawings and accompanying text show and describe particular safety syringe implementations, any such implementation may comprise any shape, size, style, type, model, version, class, grade, measurement, concentration, material, weight, quantity, and/or the like consistent with the intended operation of safety syringes.

The concepts disclosed herein are not limited to the specific safety syringe shown herein. For example, it is specifically contemplated that the components included in particular safety syringes may be formed of any of many different types of materials or combinations that can readily be formed into shaped objects and that are consistent with the intended operation of the safety syringe. For example, the components may be formed of: rubbers (synthetic and/or natural) and/or other like materials; glasses (such as fiberglass), carbon-fiber, aramid-fiber, any combination therefore, and/or other like materials; elastomers and/or other like materials; polymers such as thermoplastics (such as ABS, fluoropolymers, polyacetal, polyamide, polycarbonate, polyethylene, polysulfone, and/or the like, thermosets (such as epoxy, phenolic resin, polyimide, polyurethane, and/or the like), and/or other like materials; plastics and/or other like materials; composites and/or other like materials; metals, such as zinc, magnesium, titanium, copper, iron, steel, carbon steel, alloy steel, tool steel, stainless steel, spring steel, aluminum, and/or other like materials; and/or any combination of the foregoing.

Furthermore, safety syringes may be manufactured separately and then assembled together, or any or all of the components may be manufactured simultaneously and integrally joined with one another. Manufacture of these components separately or simultaneously, as understood by those of ordinary skill in the art, may involve 3-D printing, extrusion, pultrusion, vacuum forming, injection molding, blow molding, resin transfer molding, casting, forging, cold rolling, milling, drilling, reaming, turning, grinding, stamping, cutting, bending, welding, soldering, hardening, riveting, punching, plating, and/or the like. If any of the components are manufactured separately, they may then be coupled or removably coupled with one another in any manner, such as with adhesive, a weld, a fastener, any combination thereof, and/or the like for example, depending on, among other considerations, the particular material(s) forming the components.

In places where the description above refers to particular safety syringe implementations, it should be readily apparent that a number of modifications may be made without departing from the spirit thereof and that these implementations may be applied to other implementations disclosed or undisclosed. The presently disclosed safety syringes are, therefore, to be considered in all respects as illustrative and not restrictive.

What is claimed is:

1. A dental safety syringe comprising:
a plunger assembly having:
  a thumb ring;
  a piston rod extending from the thumb ring; and
  a harpoon on an end of the piston rod, distal to the ring;
a push lever circumscribing and slidably coupled to the piston rod, wherein a first arm of the push lever extends away from the piston rod on a left side of the piston rod and a second arm of the push lever extends away from the piston rod on a right side of the piston rod;
a carpule retainer circumscribing and slidably coupled to the piston rod, the carpule retainer positioned between the harpoon and the piston push lever; and
a carpule spring circumscribing the piston rod and positioned between the carpule retainer and the push lever, the carpule spring configured to bias the carpule retainer away from the push lever;
wherein the plunger assembly comprising an extended position wherein the thumb ring is fully extended and a compressed position wherein the thumb ring is fully compressed;
a barrel assembly detachably coupled to the plunger assembly, the plunger assembly positioned inside a first end of the barrel assembly, the barrel assembly having:
  a carpule barrel sized to receive a carpule;
  a needle adapter threadedly coupled to the carpule barrel at an end of the carpule barrel distal to the plunger assembly;
  a sliding barrel circumscribing a portion of the carpule barrel and slidably coupled to the carpule barrel;
  a first finger grip extending from the sliding barrel on a left side of the sliding barrel and second finger grip extending from the sliding barrel on a right side of the sliding barrel, each of the first finger grip and the second finger grip having a first side closest to the push lever and a second side farther away from the push lever compared to the first side;
  a trigger, positioned adjacent to the second side of the first finger grip and pivotally coupled to and extending through a finger grip collar connecting the first finger grip to the second finger grip, the trigger comprising an actuator at a first end closest the second side of the first finger grip and a latch at a second end of the trigger that extends through the sliding barrel and selectively engages with a corresponding latch of the carpule barrel;
  a push lever lock directly coupled to the second finger grip and positioned separate from the sliding barrel on the first side of the second finger grip, the push lever lock having a sloped leading edge, biased to a locked position, and configured to engage with the push lever when the push lever is pushed into an active position where the first arm and the second arm are, respectively, in contact with the first finger grip and the second finger grip; and
a safety cover detachably coupled to the sliding barrel distal to the plunger assembly and is configured to extend past a syringe needle attached to the needle adapter when the push lever is in an inactive position and expose the syringe needle when the push lever is in an active position;
wherein the safety syringe is manipulatable with a single hand from a first state in which the push lever is in the inactive position, to a second state in which the push lever is in the active position and the needle is exposed, to a third state in which contents of the carpule is expelled, and to a fourth state in which the push lever is retracted from the active position to the inactive position after the contents of the carpule is expelled.

2. The safety syringe of claim 1, wherein the needle adapter is configured to threadedly secure a syringe needle to the barrel assembly.

3. The safety syringe of claim 2, wherein the needle adapter further comprises an adapter hub configured to threadedly engage with the barrel assembly and separately engage with the syringe needle.

4. The safety syringe of claim 3, wherein the adapter hub is coupled to the carpule barrel via a threaded coupling.

5. The safety syringe of claim 1, wherein the barrel assembly further comprises:
a spring assembly coupled to the sliding barrel, the spring assembly having:
a spring barrel;
a spring positioned within the spring barrel coupled to a pair of stoppers positionally connected to the carpule barrel at a first end and to the sliding barrel at a second end;
wherein the spring is configured to be compressed when the push lever is moved from the inactive position to the active position to bias the push lever to the inactive position.

6. The safety syringe of claim 5, wherein the spring is configured to automatically return the push lever to the inactive position when the push lever lock is released, and wherein the safety cover automatically covers the syringe needle when the push lever is returned to the inactive position.

7. The safety syringe of claim 5, wherein the spring is compressed when the push lever is moved from the inactive position to the active position and the push lever is automatically secured by the push lever lock in the active position.

8. The safety syringe of claim 1, wherein the finger grip collar circumscribes the sliding barrel.

9. The safety syringe of claim 1, wherein the harpoon is configured to puncture a rubber stopper on a trailing end of the carpule to secure the plunger assembly to the carpule.

10. The safety syringe of claim 1, wherein the safety cover is coupled to the needle adapter.

11. The safety syringe of claim 1, wherein the carpule is insertable into the carpule barrel at an end of the carpule barrel opposite the needle adapter when the plunger assembly is uncoupled from the barrel assembly.

12. The safety syringe of claim 1, wherein the push lever lock includes an angled upper surface configured such that when the push lever contacts the push lever lock, the push lever lock slides to an unlocked position against a bias until an outer edge of the push lever passes the angled upper surface and the push lever lock biases to the locked position.

13. The safety syringe of claim 1, wherein the latch is configured to secure the carpule barrel to a receiver on the sliding barrel when the actuator is inactive, and wherein the actuator is configured to be depressed to unsecure the latch from the carpule barrel.

14. The safety syringe of claim 1, wherein depressing the actuator unsecures the carpule barrel from the latch, allowing the carpule barrel to slide through the sliding barrel and the safety cover to expose the syringe needle.

15. The safety syringe of claim 1, wherein the push lever is configured to be depressed by a user's thumb pressing the first arm or the second arm while squeezing the first finger grip and the second finger grip with the user's fingers.

16. The safety syringe of claim 1, wherein the syringe needle and the needle adapter are manufactured as one complete unit.

17. The safety syringe of claim 1, wherein the thumb ring, the push lever, the trigger, and the push lever lock are all operable by a user's single hand without repositioning the safety syringe in the user's single hand.

18. The safety syringe of claim 1, wherein the safety cover extends past the syringe needle when the push lever is in the inactive position.

19. The safety syringe of claim 1, wherein when the plunger assembly is removed from the barrel assembly, the carpule is removed with the plunger assembly due to the harpoon being secured to the carpule.

20. The safety syringe of claim 1, wherein the safety cover with the syringe needle enclosed therein is configured to be uncoupled from the carpule barrel and disposed of.

\* \* \* \* \*

14